United States Patent [19]

Richardson

[11] Patent Number: 4,816,026
[45] Date of Patent: Mar. 28, 1989

[54] DISPOSABLE DIAPER HAVING AN IMPROVED LEG CONFORMING CUFF

[75] Inventor: James W. Richardson, Cincinnati, Ohio

[73] Assignee: The Procter & Gamble Company, Cincinnati, Ohio

[21] Appl. No.: 66,810

[22] Filed: Jun. 25, 1987

[51] Int. Cl.⁴ ............................................. A61F 13/16
[52] U.S. Cl. .................................................. 604/385.2
[58] Field of Search ................... 604/385.2, 385.1, 386, 604/366, 370

[56] References Cited

U.S. PATENT DOCUMENTS 4,573,991 3/1986 Pieniak et al. ................ 604/385.2

Primary Examiner—John D. Yasko
Attorney, Agent, or Firm—John M. Pollaro; Fredrick H. Braun; Richard C. Witte

[57] ABSTRACT

A disposable diaper having an improved leg cuff. The disposable diaper is provided with an elastic member which is affixed to the diaper at its ends and unaffixed in its central portion. The elastic member is contained between seams having bond portions and hinge portions.

3 Claims, 1 Drawing Sheet

U.S. Patent    Mar. 28, 1989    4,816,026
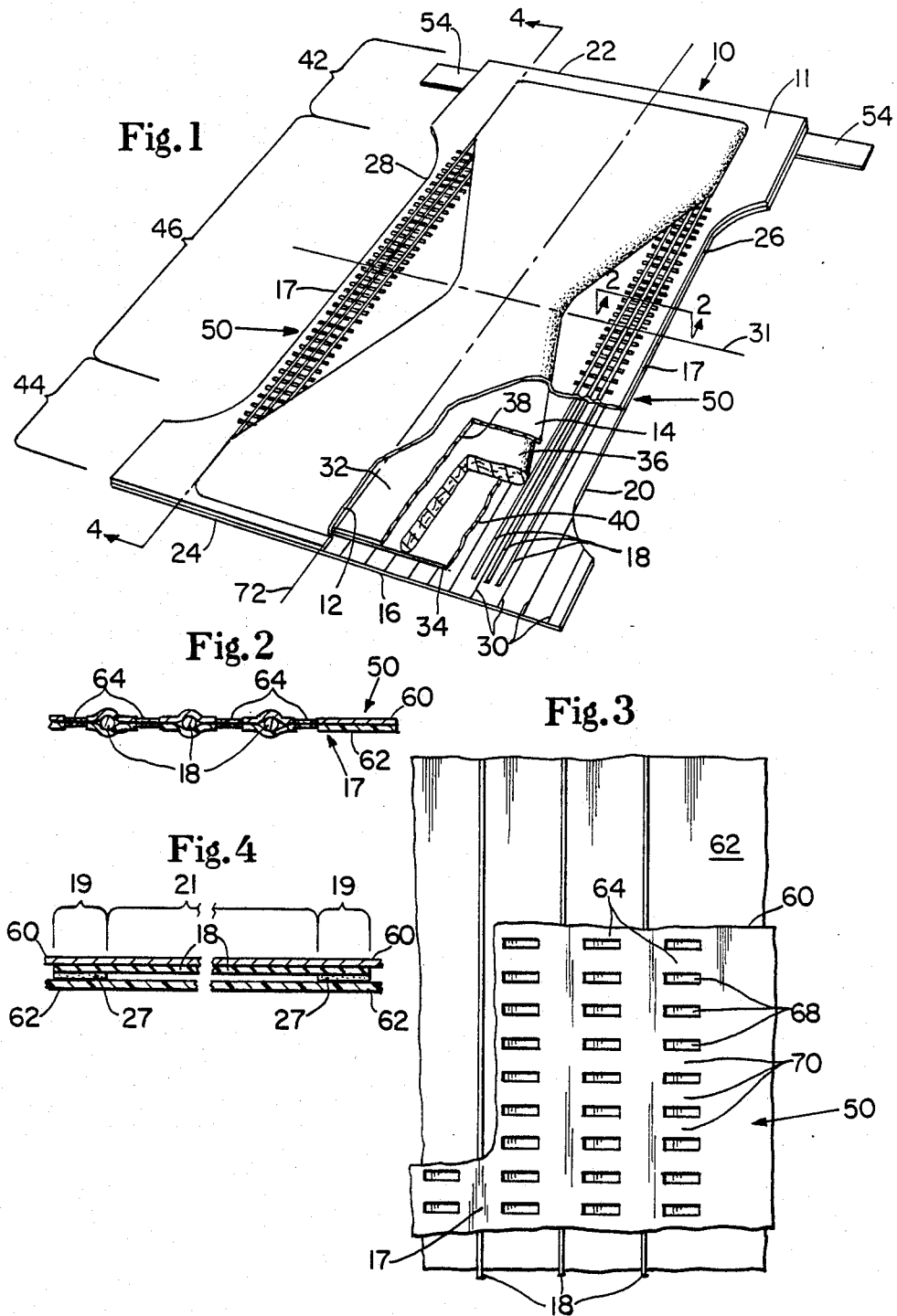

DISPOSABLE DIAPER HAVING AN IMPROVED LEG CONFORMING CUFF

BACKGROUND OF THE INVENTION

This invention relates to disposable diapers having elasticized leg openings and more particularly to disposable diapers having an improved leg conforming cuff. Still more particularly, this invention relates to an improved leg cuff iin which elastic members having an unadhered center portion are contained between seams having bond portions and hinge portions.

Disposable diapers are well known articles of manufacture which are worn by infants and incontinent persons. Disposable diapers are worn about the lower torso and are intended to absorb and contain urine and feces thereby preventing the urine and feces from soiling, wetting, or otherwise contaminating the articles (e.g., clothing, bedding, etc.) which come into contact with the diaper wearer.

In general, disposable diapers all have the same basic structure which comprises an absorbent core encased between a liquid permeable user contacting topsheet and a liquid impermeable backsheet. The prior art, or course, teaches numerous variations of and elements in addition to the basic topsheet, backsheet, and absorbent core arrangement. For example, an improvement in the performance of disposable diapers has been achieved by the addition of an elastic means along that portion of the disposable diaper which contacts the wearer's thigh thereby providing elasticized leg openings when the diaper is worn.

Typically the elastics used in the cuffs of disposable diapers are adhered to the diaper along their entire length. Thus, the elastics must develop enough contractive force to contract the topsheet, the backsheet, and the adhesive. These contractive forces are often high enough to cause irritation and red marking around the wearer's leg.

U.S. Pat. No. 3,417,751 which issued to I. L. Murdock on Dec. 24, 1968, is directed to a baby pant in which a pad overlays the elastic member to reduce discomfort and to provide a seal about the infant's legs. U.S. Pat. No. 4,081,301 which issued to K. B. Buell on Mar. 28, 1978, is directed to a method and apparatus for attaching elastic strands to a diaper in which one embodiment attaches the ends of the elastic to the diaper while leaving the center portion unadhered.

The disposable diapers of the prior art lack the aspects of the present invention whereby an improved leg cuff is provided in which the contractive force needed to gather the cuff about the wearer's leg is reduced. The reduction in the contractive force needed to gather the cuff is obtained by leaving the center portion of the elastic member unadhered to the diaper while containing the unadhered center portion between seams which have hinge portions.

It is, therefore, an object of the present invention to provide an improved leg cuff for disposable diapers.

A further object of the present invention is to provide an improved leg cuff which is gathered about the wearer's leg with reduced contractive force.

An additional object of the present invention is to provide an improved leg cuff in which the elastic members are affixed only at their ends and are contained between seams having hinge portions.

These and other objects of the invention will be more readily apparent when considered in reference to the following description and when taken in connection with the accompanying drawings.

SUMMARY OF THE INVENTION

In a particularly preferred embodiment of the present invention, a disposable diaper is provided. The diaper has elasticized longitudinal portions in which at least three elastic members are operatively associated with a cuff. The elastic members have two affixed portions which are affixed to the cuff and an unaffixed portion between the two affixed portions which is not affixed to the cuff.

The cuff has a first layer which overlays a portion of the cross sectional perimeter of the elastic members and a second layer which overlays another portion of the cross sectional perimeter. Seams affix the first layer to the second layer and are positioned adjacent to the elastic members. The seams have bond segments and hinge segments alternately positioned along the length of the seam. The first layer is affixed to the second layer at the bond segments and the first layer is unaffixed to the second layer on the hinge segments.

BRIEF DESCRIPTION OF THE DRAWINGS

While the specification concludes with claims particularly pointing out and distinctly claiming the subject matter regarded as forming the present invention, it is believed that the invention will be better understood from the following description taken in connection with the accompanying drawings in which:

FIG. 1 is a partially cut away perspective view of the disposable diaper of the present invention prior to its being folded for placement on the wearer;

FIG. 2 is a sectional view taken along section line 2—2 of FIG. 1;

FIG. 3 is a partially cut away enlarged view of a part of the elasticized longitudinal portion of the disposable diaper shown in FIG. 1; and FIG. 4 is a sectional view taken along section 4—4 of FIG. 1.

DESCRIPTION OF A PREFERRED EMBODIMENT

Referring now to the drawings, there is shown a preferred embodiment of the present invention as it would be used in a disposable diaper intended to be worn by an infant. As used herein, the term "disposable diaper" refers to a garment generally worn by infants or incontinent persons, which is drawn up between the legs and fastened about the waist of the wearer and further, which is intended to be discarded after a single use (i.e., it is not intended to be laundered or otherwise restored and reused).

FIG. 1 is a partially cut away perspective view of the disposable diaper 10 of the present invention prior to its being folded and placed on the diaper wearer by the diaper user. As can be seen in FIG. 1, a preferred diaper 10 basically comprises an outer covering layer 11, an absorbent means 14, and an elasticized longitudinal portion 17 at both longitudinal sides of the diaper 10. While the outer covering layer 11, absorbent means 14, and elasticized longitudinal portion 17 may generally be assembled in a variety of well known configurations, a preferred disposable diaper configuration is described generally in U.S. Pat. No. 3,860,003 entitled "Contractible Side Portions for Disposable Diaper", which issued to K. B. Buell on Jan. 14, 1975, which patent is incorporated herein by reference.

Still referring to FIG. 1, it can be seen that a preferred outer covering layer 11 encases and contains the absorbent means 14 and, preferably, the outer covering layer 11 comprises a topsheet 12 and a backsheet 16 which are joined together in any suitable manner, either directly to each other or indirectly through an intermediate member. FIG. 1 shows a preferred embodiment of the diaper 10 in which the topsheet 12 and the backsheet 16 are joined together directly and are coextensive having length and width dimensions generally larger than those of the absorbent means 14. The topsheet 12 is superposed on the backsheet 16 thereby forming a periphery 20 of diaper 10. The periphery 20 defines the outer periphery or, in other words, the outer extent of the diaper 10. The periphery 20 comprises first end 22, second end 24, first longitudinal side 26, and second longitudinal side 28.

The topsheet 12 may be affixed to the backsheet 16 in any suitable manner as is well known in the diaper manufacturing art. In a preferred embodiment, a multiplicity of longitudinal adhesive bands 30 of hot-melt adhesive are applied along the full length of the backsheet 16 generally parallel to the longitudinal centerline 72 of the backsheet 16. The longitudinal adhesive bands 30 serve to affix the topsheet 12 to the backsheet 16 at those points where these three components come together. The extent and location of the points where the topsheet 12, backsheet 16, and longitudinal adhesive bands 30 come together will depend on the spacing between the longitudinal adhesive bands 30 and on the distance the topsheet 12 and the backsheet 16 extend beyond the absorbent means 14. The number of longitudinal adhesive bands 30 and the spacing therebetween should be sufficient to securely bond the topsheet 12 to the backsheet 16 in the area between the periphery 20 and the edge of the absorbent means 14.

A hot-melt adhesive suitable for use as longitudinal adhesive bands 30 is manufactured by Century Adhesive Corp. of Columbus, Ohio, and marketed under the tradename R-10-A. It will be noted that the above described manner of affixing the topsheet 12 to the backsheet 16 causes the topsheet 12 to be affixed to the backsheet 16 intermittently along the first and second ends, 22 and 24. The absorbent means 14 is thereby encased between the topsheet 12 and the backsheet 16. Of course, many alternative methods of affixing the topsheet 12 or the backsheet 16 may be used with satisfactory results. For example, the topsheet 12 may be affixed to the backsheet 16 indirectly rather than directly as is shown in FIG. 1. Thus, an intermediate member may be used to affix the topsheet 12 to the backsheet 16.

The diaper 10 has first and second waist portions 42 and 44 extending, respectively, from the first end 22 and the second end 24 of the diaper periphery 20 toward the lateral centerline 31 of the diaper 10 a distance from about 1/5 to about ⅓ the length of the diaper. The waist portions 42 and 44 comprise those portions of the diaper 10 which, when worn, encircle the waist of the wearer. The crotch portion 46 is that portion of the diaper 10 between first and second waist portions 42 and 44, and comprises that portion of the diaper 10 which, when worn, is positioned between the legs of the wearer and covers the lower torso of the wearer.

The absorbent means 14 may be any means which is generally compressible, conformable, non-irritating to the wearer's skin, and which is capable of absorbing and retaining liquids. A preferred absorbent means 14 has first and second opposed faces 32 and 34 respectively and comprises an absorbent layer 36 and first and second tissue layers 38 and 40, respectively. The first and second tissue layers 38 and 40 overlay the major surfaces of the absorbent layer 36 to form the first and second opposed faces 32 and 34 of the absorbent means 14.

The absorbent layer 36 is intended to absorb and contain liquid and may be manufactured in a wide variety of sizes and shapes (e.g., rectangular, hourglass, etc.) and from a wide variety of liquid absorbent materials commonly used in disposable diapers, such as comminuted wood pulp which is generally referred to as airfelt. Other liquid absorbing materials may also be used in the manufacture of the absorbent layer 36 such as a multiplicity of plies of creped cellulose wadding, absorbent gelling material, absorbent foams or sponges, or any equivalent material or combination of materials. The total absorbent capacity of the absorbent layer 36 should, however, be compatible with the design liquid loading in the intended use of the disposable diaper 10. Further, the size and absorbent capacity of the absorbent layer 36 may be varied to accommodate wearers ranging from infants through adults.

The preferred embodiment of diaper 10 illustrated in FIG. 1 has an hourglass shaped absorbent layer 36, and is intended to be worn by infants ranging in weight from about 12 to about 26 pounds (about 5 kgs. to about 12 kgs). The absorbent layer 36 is, therefore, a batt of airfelt approximately 16 inches (41 cm) long when measured along the longitudinal centerline 72, approximately 6.5 inches (16 cm) across the first and second ends 22 and 24, and approximately 5 inches (13 cm) across the narrowest part of the crotch portion 46. The absorptive capacity of the airfelt used for the absorbent layer 36 is sufficient to absorb and retain from about 8 to about 16 grams of water per gram of absorbent material. Accordingly, the airfelt used in the preferred embodiment shown in FIG. 1 weighs from about 15 to about 56 grams and has a generally uniform caliper. It should be understood, however, that the size, shape configuration, and total absorbent capacity of the absorbent layer 36 may be varied to accommodate wearers ranging from infants through adults. Therefore, the dimensions, shape, and configuration of the absorbent layer 36 may be varied (e.g. the absorbent layer 36 may have a varying caliper, or a hydrophillic gradient, or may contain absorbent gelling materials).

The first and second tissue layers, 38 and 40, are intended to improve the tensile strength of the absorbent core 14 and to reduce the tendency of the absorbent layer 36 to split, lump or ball when wetted. The first and second tissue layers, 38 and 40, also help to improve lateral wicking of liquids, thereby providing a more even distribution of liquid in the absorbent layer 36. While a number of materials and manufacturing techniques may be used to manufacture the first and second tissue layers, 38 and 40, satisfactory results have been obtained with sheets of tissue paper having a basis weight of approximately 10 pounds per 3000 square feet (16 gms per square meter) and having an air permeability of approximately 100 cubic feet per minute per square foot (30 cubic meters per minute per square meter) over a 0.5 inch (13 mm) water pressure drop. While the first and second tissue layers, 38 and 40, are preferably coterminous with the absorbent layer 36, they may have different dimensions, a different configuration, or they may be omitted entirely.

The absorbent means 14 is superimposed on the backsheet 6 and is preferably affixed thereto by any means as is well known in the diaper art. For example, the absorbent core 14 may be secured to the backsheet 16 by a uniform continuous layer of adhesive, a patterned layer of adhesive, or any array of lines or spots of adhesive. In the preferred embodiment illustrated in FIG. 1 the longitudinal adhesive bands 30 are used to affix the absorbent core 14 to the backsheet 16.

The backsheet 16 is impermeable to liquids and prevents liquids absorbed by the absorbent means 14 from wetting the undergarments, clothing, bedding, and other objects which contact the wearer of the disposable diaper 10. Preferably the backsheet 16 is a polyethylene film of from about 0.005 to about 0.002 inches (about 0.012 to about 0.051 mm) thick, although other flexible, liquid impermeable materials may also be used. As used herein, the term "flexible" refers to materials which are compliant and which readily conform to the shape and contours of the human body. A suitable polyethylene film is manufactured by Monsanto Chemical Company and marketed in the trade as Film No. 8020. The backsheet 16 is preferably embossed and/or matte finished to provide a more clothlike appearance. Further, the backsheet 16 may have passages which permit vapors to escape from the absorbent means 14 while still preventing liquid from passing through the backsheet 16. In a preferred embodiment, the backsheet 16 has a modified hourglass shape extending beyond the absorbent layer 36 a minimum distance of at least about 0.5 inches (about 1.3 cm) around the entire diaper periphery 20.

The topsheet 12 is compliant, soft feeling, and non-irritating to the wearer's skin and prevents the wearer of the diaper 10 from contacting the absorbent core 14. Further, the topsheet 12 is liquid permeable permitting liquids to readily penetrate through its thickness. A suitable topsheet 12 may be manufactured from a wide range of materials, such as natural fibers (e.g., wood or cotton fibers), synthetic fibers (e.g., polyester, polyethylene, polypropylene), or a combination thereof. Alternatively, the topsheet 12 may be a foam, such as the reticulated foams which are well known in the art or any of the formed films which are also well known in the art.

A number of manufacturing techniques can be used to manufacture the topsheet 12. For example, the topsheet 12 may be woven, nonwoven, spunbonded, carded, or the like. A preferred topsheet 12 is carded, and thermally bonded by means well known to those skilled in the nonwoven fabrics art. Preferably the topsheet 12 has a weight of from about 18 to about 25 grams per square yard, a minimum dry tensile strength of at least about 400 grams per centimeter in the machine direction and a wet tensile strength of at least about 55 grams per centimeter in the cross machine direction.

A cuff 50 is positioned along the first longitudinal side 26 and another cuff 50 is positioned along the second longitudinal side 28. In general, the cuffs 50 comprise the portion between the first and second longitudinal sides 26 and 28 and the corresponding longitudinal side of the absorbent means 14. The cuffs 50 are gatherable areas which may be either unitary (i.e., cuff 50 has at least one continuous and undivided element in common with the outer covering layer) or integral (i.e., the cuff 50 is a separate element affixed to the rest of the diaper 10) with the outer covering layer 11. Referring now to FIGS. 2, 3, and 4, it can be seen that in the preferred embodiment illustrated the cuff 50 comprises a first layer 60 and a second layer 62. In the preferred embodiment illustrated in the FIG.s, the cuffs 50 are unitary with the outer covering layer 11 and the first layer 60 is formed by extending the topsheet 12 beyond the edge of the absorbent means 14 and the second layer 62 is formed by extending the backsheet 16 beyond the edge of the absorbent means 14.

Each elasticized longitudinal portion 17 comprises at least three elastic members 18 which are operatively associated with each cuff 50 in the crotch portion 46 in an elastically contractible condition so that in a normally unrestrained configuration, the elastic members 18 effectively contract or gather the cuff 50. As used herein the term "operatively associated" refers to two or more components which act together. In the preferred embodiment shown in the FIG.s, the elastic in members 18 are positioned between the first layer 60 and the second layer 62 and are operatively associated with both cuffs 50 in the crotch portion 46. Thus, the elastic members 18 are affixed to the cuffs 50 so as to cause the cuffs 50 to contract when the elastic members 18 are allowed to contract.

Referring specifically to FIG. 4, it can be seen that the elastic members 18 each have two affixed portions 19 and an unaffixed portion 21 between the two affixed portions 19. The affixed portions 19 of the elastic members 18 are affixed to the cuff 50 and the unaffixed portion 21 is unaffixed to the cuff 50. For example, the affixed portions 19 may be affixed to the second layer 62 using an adhesive bead 27. A suitable method for incorporating elastic members 18 into a disposable diaper is described in U.S. Pat. No. 4,081,301 entitled "Method and Apparatus for Continuously Attaching Discrete, Stretched Elastic Strands to Predetermined Isolated Portions of Disposable Absorbent Products" which issued to K. B. Buell on Mar. 28, 1978, and which patent is incorporated herein by reference.

Referring specifically to FIGS. 2 and 3, it can be seen that the elastic members have a cross sectional perimeter and that the first layer 60 overlays at least a portion of the cross sectional perimeter of the elastic members 18 and the second layer 62 overlays another portion of the cross sectional perimeter of the elastic members 18. The first and second layers 60 and 62 are affixed to each other along a plurality of seams 64. The seams 64 are positioned along the longitudinal sides of the elastic members 18 at least in a segment of the unaffixed portion 21 and comprise bond segments 68 and hinge segments 70 alternately placed along the length of the seams 64. The bond segments 68 serve to bond the first layer 60 and the second layer 62 together, thereby confining at least a portion of the unaffixed portion 21 of the elastic members 18 between two of the seams 64.

The bond segments 68 may be formed in a number of ways that will suggest themselves to one skilled in the art. For example, the bond segments 68 may be formed by gluing the first layer 60 to the second layer 62. In the preferred embodiment shown in the FIG.s, the bond segments 68 are formed by heat sealing the first layer 60 to the second layer 62. The bond segments 68 have sufficient strength to maintain the attachment between the first and second layers 60 and 62. The bond segments 68 are relatively rigid and are not readily contracted by the elastic members. Thus, if the dimension of the bond segments 68 in a direction parallel to longitudinal center line 72 is too long, the elasticized longitudinal portion 17 will require relatively high contractive forces to gather the cuff 50. It has been found that the length of the bond segment is preferably less than about 10 cm.

In the hinge segments 70, the first and second layers 60 and 62 are unbonded to each other and the hinge segments 70, therefore, remain flexible. Thus, as the cuffs 50 are gathered by the elastic members 18, the hinge segments 70 permit the first and second layers 60 and 62 to buckle, thereby reducing the contractive force needed to gather the cuffs 50. The hinge segments 70 have a length which is short enough to prevent the elastic members 18 from becoming interposed between the bond segments 68. It has been found that hinge segments 70 having a length less than about 5 cm work well.

In the preferred embodiment illustrated, the elastic members 18 are operatively associated with the cuffs 50 by being affixed to the cuffs 50 using a suitable adhesive which will be of sufficient adhesiveness to hold the elastic members 18 to the cuff 50 while the elastic members 18 are stretched. An adhesive which has been used with satisfactory results in manufactured by Findley Adhesives Corporation of Elm Grove, Wis., and is marketed under the trade name Findley H-2031-01.

Suitable elastic members 18 may be manufactured from a wide variety of elastic materials such as natural rubber, or elastomeric films such as Kraton, ethylene propylene-dimonomer, and polyurethane. The elastic members 18 can be operatively associated with the cuffs 50 in an elastically contractible condition in at least two ways. For example, the elastic member 18 may be stretched and while in the stretched condition affixed to the uncontracted and unstretched cuffs 50. Alternatively, the cuffs 50 may be contracted (e.g., by pleating) and then affixing the unstretched elastic member 18 to the contracted cuffs 50.

In addition, the elastic members 18 may take a multitude of configurations. For example, the width of the elastic members 18 may be varied from about 0.015 inches to 1.0 inches (0.38 mm 25 mm) or more; or the elastic members 18 may be rectilinear or curvilinear. Still further, the elastic members 18 may be affixed to the diaper 10 in any of several ways which are well known in the art. For example, the elastic members 18 may be ultrasonically bonded or heat sealed into the cuffs 50 using a variety of bonding patterns or the elastic members 18 may simply be glued to the cuffs 50.

One material which has been found to work well as an elastic member 18 is an elastic thread having a cross section of 0.017 inches by 0.019 inches (about 0.43 mm by about 0.48 mm) and which is manufactured from natural rubber. Such a product is marketed by Fulflex under the trade name 9212. The preferred elastic member 19 produces a tensile force of about 100 grams when stretched 100 percent from its relaxed condition.

The diaper 10 is provided with a fastening means 54 for maintaining the first and second waist portions 42 and 44 in an overlapping configuration when the diaper 10 is worn (see FIG. 1). Thus, the diaper 10 is fitted to the wearer and a side closure formed.

More specifically, the fastening means 54 affixes the first waist portion 42 to the second waist portion 44 thereby maintaining the first and second waist portions 42 and 44 in an overlapping configuration. Thus, the fastening means 54 must be affixed to both the first waist portion 42 and the second waist portion 44 in a manner and with a strength that is sufficient to resist the forces acting to cause the first and second waist portions 42 and 44 to separate during wearing.

The fastening means 54 may comprise any of the well known means for achieving a side closure such as Velcro strips or patches, buttons, or snaps. A preferred fastening means 54 is an adhesive tape as is well known in the diaper art.

What is claimed is:

1. A disposable diaper comprising:
   an outer covering layer;
   an absorbent means for absorbing liquids, said absorbent means being encased within said covering layer;
   elasticized longitudinal portions at both longitudinal sides of the diaper, said elasticized longitudinal portions having a cuff and at least three individual and uninterconnected elastic members operatively associated with said cuff in an elastically contractible condition, said elastic members having a cross sectional perimeter, two affixed portions and an unaffixed portion between said two affixed portions, said cuff having a first layer overlapping a portion of said cross sectional perimeter and said second layer overlapping another portion of said cross sectional perimeter, said two affixed portions of said elastic being affixed to said cuff and said affixed portion of said elastic being unaffixed to said cuff; and
   seams affixing said first layer to said second layer, said seams being positioned adjacent to said elastic members and having bond segments and hinge segments alternately positioned along the length of said seams, said first layer being affixed to said second layer at said bond segments and said first layer being unaffixed to said second layer at said hinge segments.

2. The disposable diaper of claim 1 wherein said bond segments have a length less than about 10 cm and said hinge segments have a length less than about 5 cm.

3. The disposable diaper of claim 1 wherein said seams are positioned adjacent to said elastic members only at the unaffixed portion of said elastic members.

* * * * *

UNITED STATES PATENT AND TRADEMARK OFFICE
CERTIFICATE OF CORRECTION

PATENT NO. : 4,816,026

DATED : March 28, 1989

INVENTOR(S) : James W. Richardson

It is certified that error appears in the above-identified patent and that said Letters Patent is hereby corrected as shown below:

Column 2, at line 40:    delete "section 4--4" and insert -- section line 4--4 --

Column 5, at line 4:    delete "6" and insert -- 16 --

Column 8, at line 1:    delete "19" and insert -- 18 --

Signed and Sealed this

Fourteenth Day of November, 1989

*Attest:*

JEFFREY M. SAMUELS

*Attesting Officer*      *Acting Commissioner of Patents and Trademarks*